(12) United States Patent
Navot et al.

(10) Patent No.: US 6,348,640 B1
(45) Date of Patent: *Feb. 19, 2002

(54) TAMPON DETECTION SYSTEM

(76) Inventors: Nir Navot, 1 Hapaamon Street, Rosh Haayin; Ronnie Botton, 8 Tabenkin Street, Herzlia, both of (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/508,966

(22) PCT Filed: Sep. 28, 1998

(86) PCT No.: PCT/US98/20257

§ 371 Date: Mar. 20, 2000

§ 102(e) Date: Mar. 20, 2000

(87) PCT Pub. No.: WO99/17692

PCT Pub. Date: Apr. 15, 1999

Related U.S. Application Data

(63) Continuation of application No. 08/943,193, filed on Oct. 3, 1997, now Pat. No. 5,904,671.

(51) Int. Cl.⁷ .............................................. A61F 13/15
(52) U.S. Cl. ................. 604/361; 604/904; 604/385.18; 73/73; 340/573; 340/604
(58) Field of Search ................................. 604/361, 363, 604/904, 385.17, 385.18; 73/73; 340/604, 573

(56) References Cited

U.S. PATENT DOCUMENTS

| | | | | |
|---|---|---|---|---|
| 3,794,024 A | * | 2/1974 | Kokx et al. | 604/361 |
| 4,800,370 A | * | 1/1989 | Vetecnik | 340/573 |
| 5,395,358 A | * | 3/1995 | Lu | 604/361 |
| 5,469,146 A | * | 11/1995 | Gurler | 340/605 |
| 5,557,263 A | * | 9/1996 | Fisher et al. | 340/605 |
| 5,904,671 A | * | 5/1999 | Navot et al. | 604/361 |
| 6,063,042 A | * | 5/2000 | Navot et al. | 600/584 |

* cited by examiner

Primary Examiner—Dennis Ruhl
(74) Attorney, Agent, or Firm—Mark M. Friedman

(57) ABSTRACT

This invention is a tampon wetness detection system which includes a housing (70) having a distal end, a proximal end, the proximal end being shaped, and dimensioned for insertion into a distal end of an absorbent body (12) inserted into a vagina, and the proximal end of the housing being fluid permeable; a radio frequency identification device (16) being implemented in the housing, and the radio frequency device including a transmitter (18); a conductive wetness sensor (20) being in the proximal end of the housing, and in electrical communication with the radio frequency identification device such that when the conductive wetness sensor senses wetness the radio frequency identification device is operable; a remote reporting device including a receiver for receiving a radio signal concerning the wetness of the absorbent body from the radio frequency identification device, and further including a reporting mechanism for reporting a user of the wetness of the absorbent body.

9 Claims, 2 Drawing Sheets

TAMPON DETECTION SYSTEM

This application is a national stage of PCT/US98/20257 filed Sep. 28, 1998, which is a continuation of Ser. No. 08/943,193 filed Oct. 3, 1997 now U.S. Pat. No. 5,904,671.

FIELD AND BACKGROUND OF THE INVENTION

The present invention relates to tampons, and more particularly to a tampon wetness, substances and other parameters detection system signaling a remote-reporting device of the wetness of the tampon, of presence and/or concentration of specific the substances and/or the parameters magnitude. The remote-reporting device according to preferred embodiments of the present invention not only alerts the user of the present condition of the tampon, rather it also records for later retrieval and analysis information for research, diagnosis and treatment, if so required.

Present-day users of tampons have to use a destructive test in order to ascertain whether a tampon has residual absorbent capacity remaining. That is, the tampon must be removed to see if it is full, and even if it is not full, the tampon is not reinserted. Generally a user removes a tampon before it has reached its capacity in order to prevent an accident wherein the capacity of the tampon is exceeded and the excess menses flows unimpeded from the vagina to soil the user's clothing.

In tampons as presently known, a determinative criterion frequently used for removing a tampon is time elapsed since insertion. The time elapsed criteria for changing tampons is not satisfactory for several reasons, e.g., the menstrual flow rate varies throughout the menstruating period and much adsorbent capacity of tampons is wasted due to the tendency to change before an accident occurs.

The flow variation throughout the period causes problems as to how long to wear a tampon because a user cannot establish a definite time period for which the absorbent capacity within a tampon is sufficient. Therefore, she is in a quandary as to how long to wear specific tampons during days of heavy flow as contrasted to day of light flow.

A correlation between tampon performance during light flow versus heavy flow is difficult for the user to make. Thus, since the user would rather be safe than sorry, she frequently removes a tampon before the absorbent capacity of the tampon has been reached and wastes much of the product she had purchased.

The prior tampon art tried to make tampons bigger and more absorbent so that a user would not have to change as often. But the user would still waste a portion of the absorbent capacity she had purchased in that she still was not willing to have an accident.

Therefore, bigger tampons provided a longer wearing time but did not approach the problem of fully using the absorbent capacity within a tampon without soiling her clothing. In rare cases, should a user forget to remove a tampon a life threatening infection may develop.

These problems associated with the use of tampons were recognized and solutions proposed.

U.S. Pat. No. 3,794,024 to Kokx discloses an indicator in contact with the absorbent body of a catamenial device. The indicator "reads" the wetness of the absorbent body and translates the wetness into a signal, which can be sensed without removing the catamenial device. Change in temperature (heat generation or consumption by dissolving material) or color formation are used as indicators.

However, both these approaches suffer limitations. The amount of heat generated or consumed depends upon the reaction rate. If it is slow, heat dissipation will prevent sensing the signal. Color indication, on the other hand, requires an intimate inspection by the user.

U.S. Pat. No. 5,361,627 to Levesque discloses a method and apparatus for measuring the capillary attraction developed at a surface of an absorbent body intended to be used in a sanitary article such as a sanitary napkin, a diaper, a urinary pad, an adult brief, a tampon or a wound dressing, among others. The apparatus comprises a probe of fritted glass providing an array of capillary passageways in fluid communication with the interior of a closed cell completely filled with liquid. A pressure sensor mounted to the closed cell observes the liquid pressure therein. When the probe is placed in contact with the absorbent body, the capillary attraction exerted on liquid in the probe capillaries by the porous network of the absorbent body is transmitted through the liquid medium in the cell to the pressure sensor. The pressure data thus obtained reflects the state of dryness of the absorbent body surface. The capillary attraction measurement is made with no appreciable transfer of liquid toward the absorbent body to avoid altering its condition.

While the invention by Levesque is suitable of measuring the capillary attraction developed at the surface of externally used absorbent bodies, it is not at all applicable for a vaginally inserted tampon. Furthermore, a wetness test using the disclosed device requires intimacy.

U.S. Pat. No. 5,468,236 to Everhart discloses a disposable feminine care product which includes a chemically reactive means having an end point adapted to provide a visual indication of the presence of a substance in mammalian bodily excrement. However, a wetness test using the disclosed device requires intimacy.

Similar solutions, which include visual indication of the wetness of the tampon, are disclosed in U.S. Pat. Nos. 4,192,311 to Felfoldi; and 5,217,444 to Schoenfeld.

Visual indications of wet diapers are disclosed in U.S. Pat. Nos. 3,952,746 to Summers; 4,231,370 to Mroz; 4,287,153 to Towsend; 4,327,731 to Powell; 4,507,121 to Leung; 4,705,513 to Sheldon et al.; 4,738,674 to Todd et al.; and 5,197,958 to Howell.

Conductivity based indication of wet diapers are disclosed in U.S. Pat. Nos. 5,266,928 and 5,469,145 to Johnson; 4,205,672 to Dvorak; 4,484,573 to Yoo; 4,704,108 to Okada; 4,796,014 to Chia; and 5,568,128 to Nair. U.S. Pat. Nos. 4,356,818 to Macias et al.; 4,653,491 and 4,754,264 to Okada et al. disclose remote wetness informing device using an oscillator and receiver.

There is thus a widely recognized need for, and it would be highly advantageous to have, a tampon wetness detection system devoid of the above limitations, which is also useful in collecting information of vaginal secretions.

SUMMARY OF THE INVENTION

According to the present invention there is provided a detection system which can be assembled in a tampon and be used to provide a remote-reporter with information regarding the wetness of the tampon, its remaining absorbent capacity, and the concentration of various substances and the magnitude of various parameters in vaginal secretions.

According to further features in preferred embodiments of the invention described below, the system comprising (a) a housing having a distal end and a proximal end, the proximal end being shaped and dimensioned insertable into a distal end of a tampon, the proximal end of the housing being fluid permeable; (b) a radio frequency identification device being in the housing, the radio frequency identification device including a transmitter; (c) a conductive wetness sensor being in the proximal end of the housing and in electrical communication with the radio frequency identification device, such that when the conductive wetness sensor senses wetness the radio frequency identification device is operable; and (d) a remote-reporting device including a receiver for receiving a radio signal concerning the wetness of the tampon from the radio frequency identification device and further including a reporting mechanism for reporting a user of the wetness of the tampon.

According to still further features in the described preferred embodiments the housing has a shape of a thumb tack (nail).

According to further features in preferred embodiments of the invention described below, the system comprising (a) a tampon assembly including (i) an absorbent body insertable into a vagina; (ii) a radio frequency identification device being implemented in contact with the body, the radio frequency identification device including a transmitter; and (iii) a conductive wetness sensor being implemented in intimate contact with the body, the conductive wetness sensor being in electrical communication with the radio frequency identification device, such that when the conductive wetness sensor senses wetness the radio frequency identification device is operable; and (b) a remote-reporting device including a receiver for receiving a radio signal concerning the wetness of the tampon from the radio frequency identification device and further including a reporting mechanism for reporting a user of the wetness of the tampon.

According to still further features in the described preferred embodiments the tampon assembly further includes a plurality of conductive wetness sensors being implemented in intimate contact with and along the body, each of the plurality of conductive wetness sensors being in electrical communication with the radio frequency identification device, such that when any of the conductive wetness sensors senses wetness the radio frequency identification device is operable for providing a sensor specific radio signal, so that information of tampon available wetness capacitance is obtainable.

According to still further features in the described preferred embodiments any of the systems further comprising a remote-prompting device for promoting the radio frequency identification device to transmit the radio signal.

According to still further features in the described preferred embodiments the remote-reporting device and the promoting device are integrated into a remote-reporting and prompting device.

According to still further features in the described preferred embodiments the radio frequency identification device of any of the above systems is selected from the group consisting of passive radio frequency identification device and active radio frequency identification device.

According to still further features in the described preferred embodiments the conductive wetness sensor of any of the above systems include two spaced metal plates (electrodes) and an absorbent substance disposed therebetween, such that when the absorbent substance becomes wet, the sensor becomes conductive.

According to another embodiment there is provided a tampon assembly comprising (a) an absorbent body insertable into a vagina; (b) a radio frequency identification device being implemented in contact with the body, the radio frequency identification device including a transmitter; and (c) a sensor being implemented in contact with the body, the sensor being in electrical communication with the radio frequency identification device, such that when the sensor senses a substance or parameter the radio frequency identification device is operable.

According to yet another embodiment there is provided a system for detecting a substance or a parameter of a body fluid comprising (a) a tampon assembly comprising (i) an absorbent body insertable into a vagina; (ii) a radio frequency identification device being implemented in contact with the body, the radio frequency identification device including a transmitter; and (iii) a sensor being implemented in contact with the body, the sensor being in electrical communication with the radio frequency identification device, such that when the sensor senses a substance or parameter the radio frequency identification device is operable; and (b) a reporting device including a receiver for receiving a radio signal from the radio frequency identification device and further including a reporting mechanism for reporting a user of the wetness of the tampon.

According to still further features in the described preferred embodiments the sensor is in intimate contact with the absorbent body and further wherein the radio frequency identification device communicated with the sensor via a wire.

According to still further features in the described preferred embodiments the sensor communicates with the absorbent body via a capillary string and further wherein the sensor and the radio frequency identification device are integrated into a single device connected to the string.

The present invention successfully addresses the shortcomings of the presently known configurations by providing a detection system that can be assembled in a tampon and be used to provide a remote-reporter with information concerning the wetness of the tampon, its remaining capacity, concentration of substances and magnitude of parameters in vaginal secretion.

One object of the present invention is to provide a tampon which can be worn until essentially all of the absorbent capacity of a tampon is depleted.

It is another object of the present invention to provide a tampon having a sensor which senses wetness in at least the last effective portion of the tampon and transmits its readings upon request to a remote-reporter, thereby to avoid the need for intimate inspection by the user.

It is yet another object of the present invention to provide a tampon having a sensor which senses substances and/or parameters of vaginal secretions and transmits its readings upon request to a reporter.

BRIEF DESCRIPTION OF THE DRAWINGS

The invention herein described, by way of example only, with reference to the accompanying drawings, wherein.

DESCRIPTION OF THE PREFERRED EMBODIMENTS

Figure 1:
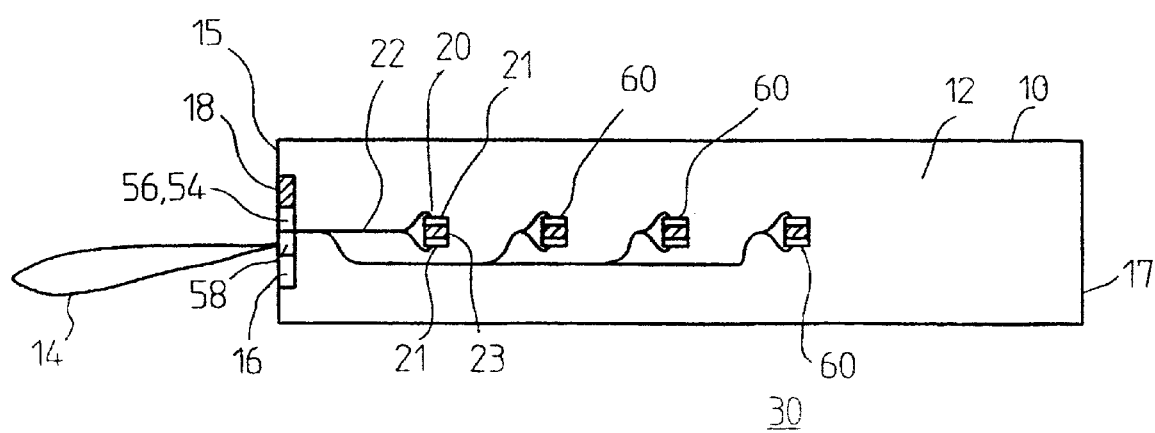
FIGS. 1 and 2 are simplified schematic depictions of components of a tampon wetness detection system according to one embodiment of the present invention.

The present invention is of a tampon detection system which can be assembled in a tampon and be used to provide a remote-reporter with information concerning, for example, a presence of a change in concentration of one or more specific substances, such as, but not limited to, menses, blood, water, sugars, minerals, ions, salts, proteins, toxins, microorganisms, and the like, or to one or more parameters, such as, but not limited to, temperature, wetness, pH and the like. Specifically, the present invention can be used to provide a user with information concerning the remaining capacity of the tampon and whether the tampon's capacity is exhausted or nearly exhausted and the tampon is to be removed. An important feature of the present invention is that it diminished the need for intimate inspection by the user.

the principles and operation of a tampon detection system according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 illustrates a tampon assembly according to the present invention, referred to hereinbelow as tampon assembly 10.

Tampon assembly 10 includes an absorbent body 12 insertable into a vagina of a user. Body 12, is typically mad of a rolled and compressed absorbent material, such as cottonwool, covered by non-woven material. Body 12 is cylindrical, and is preferably equipped with a removing floss 14 at its distal end 15.

Tampon assembly 10 further includes a radio frequency identification device 16. Device 16 is implemented in contact with (e.g., in, on, loose contact, indirect contact, etc.) body 12. Radio frequency identification device includes a transmitter 18.

Tampon assembly 10 further includes a conductive wetness sensor 20. Sensor 20 is implemented in intimate contact with (e.g., in) body 12 and is in electrical communication 22 with radio frequency identification device 18. When conductive wetness sensor 20 senses wetness, radio frequency identification device 16 is operable (i.e., operated or being capable of operation).

Conductive wetness sensor 20 preferably includes two metal plates 21 and an absorbent substance 23 intimately disposed therebetween, such that when absorbent substance 23 becomes wet, sensor 20 becomes conductive.

Menses is deposited in the vagina from the cervix of the uterus and flows downward in the vagina toward the introitus. Thus the proximal end 17 of absorbent body 12 becomes wetted first, and, in addition, the bottom surface of body 12 wets before the top surface due to the tendency of menses to flow along the floor of the vagina.

Therefore, absorbent body 12 becomes wetted progressively from the proximal end 17 toward the distal end 18 and from the bottom toward the top. This wetting pattern leaves the distal end 15 as the last area of an absorbent body 12 to be wetted.

Since the function of sensor 20 is to sense impending failure, it is preferably in contact with absorbent body 12 in the area which is wetted just prior to failure, i.e., close or at distal end 15 of the absorbent body 12.

Figure 2:
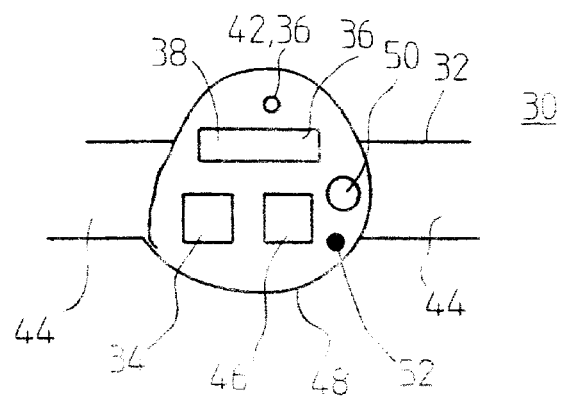

With reference to FIGS. 1 and 2, further according to the present invention provided is a system for detecting wetness of a tampon, referred to hereinbelow as system 30.

System 30 includes a tampon assembly 10 as hereinabove described with respect to FIG. 1. System 30 further includes a remote-reporting device 32. Reporting device 32 includes a receiver 34 for receiving a radio signal concerning the wetness of body 12 from radio frequency identification device 16.

Remote-reporting device 32 further includes a reporting mechanism 36 for reporting a user of the wetness of body 12. Reporting mechanism may acquire many forms. For example, reporting mechanism 36 may be a display 38, such as a liquid crystal display (LCD). Alternatively, reporting mechanism 36 may be a light source 40, such as a light emitting diode (LED) 42. In addition, reporting mechanism may be a vibrator or a sound alarm.

In a preferred embodiment reporting mechanism 36 includes more than one reporting mode and a mode selector is provided to enable a user to select a desired reporting mode, for example, awakening modes (vibration or sound) during night time and intimate or personal modes (display, light or vibration) during day time.

Radio frequency device 16 thus communicates via transmitter 18 with receiver 34 of remote-reporting device 32. Remote-reporting device 32 is a portable device carried by a user. In a preferred embodiments it includes wristbands 44 (proximal parts of which are shown) and may therefore be worn on a wrist of the user.

In a preferred embodiment of the invention system 30 further includes a remote-prompting device 46. Prompting device serves for promoting radio frequency identification device 16 to an operable state. In this case, transmitter 18 of device 16 may operate only upon command received via prompting device 46. The use of a prompting device is presently preferred since it allows a user to choose a convenient moment to be reported.

In a preferred embodiment of the invention remote-reporting device 30 and promoting device 46 are integrated under a single housing into a remote-reporting and prompting device 48.

Device 48 includes a power source 50 for its operation. Power source provides the power required for the operation of receiver 34, reporting mechanism(s) 36 and prompting device 46. Device 48 preferably further includes an on/off control button 52.

As well known from the art of smart cards two families of radio frequency identification devices are known. These include passive radio frequency identification devices and active radio frequency identification devices.

Passive devices use a capacitor as a source of power. The capacitor is charged by a remote radio transmitter (a prompting device). Upon discharge, the capacitor provides power to a radio transmitter which transmits relevant data to a remote receiver.

Active radio frequency identification devices include a self-sustained power source (battery) which provides the transmitter with power for operation. Such devices typically further include a receiver for receiving a promoting signal from a remote-prompting transmitter, such that battery power may be saved. The power source can be made removable for reuse.

Information concerning the operation of both active and passive radio frequency identification devices is found in Smart Card Technology International, The Global Journal of Advanced Card Technology, Robin Townend et al., Eds. GLOBAL PROJECTS GROUP 11/15 Betterton St., Covent Garden, London, 1996; and CardTech/SecureTech, Proceedings of the CardTech/SecureTech 1996 conference, Atlanta, Ga., May, 1996, both are incorporated by reference as if fully set forth herein.

Thus, depending on the specific application, if device 16 is selected active, it includes a battery 54, whereas if device 16 is selected passive, it includes a capacitor 56, both serve as a source of power for the operation of transmitter 18 of device 16.

In the first case, i.e., if device 16 is selected active, it preferably further includes a prompting receiver 58 to receive a prompting signal from prompting device 46. In the second case, however, prompting device 46 operates by affecting capacitor 56.

The operation of system 30 is as follows. A user inserts assembly 30 into her vagina, such that body 12 is capable of absorbing menses.

When absorbent layer 23 of sensor 20, which is in intimate contact with absorbent body 12, becomes wet, sensor 20 becomes conductive and an electrical circuit is closed.

Prompting device 16 when sensor 20 is not conductive results is no response for a passive device 16 since, under such circumstances capacitor 56 is not chargeable, or in either no response or a negative response for an active device 16 which is battery operated.

On the other hand, prompting device 16 when sensor 20 is conductive results is a signal transmitted by transmitter 18 of device 16 to receiver 34 of device 32 or 48.

One ordinarily skilled in the art would know how to devise and assemble the above components of system 30 according to the present invention.

The above-described system is suitable for providing a yes or no answer with respect to free absorbent capacitance of a tampon. It may, however, be desirable to provide system 30 with a plurality of additional conductive wetness sensors 60 implemented in intimate contact with and along body 12. Like sensor 20, each of wetness sensors 60 is in electrical communication with radio frequency identification device 16, such that when any of conductive wetness sensors 20 or 60 senses wetness, radio frequency identification device 16 is operable for providing a sensor specific radio signal, so that information of body's 12 remaining absorbent capacitance is obtainable.

In this case device 16 should be acquired the ability to differentiate among the different sensors 20 and 60. This could, for example, be achieved by providing device 16 with plurality of transmitters, each associated with a different sensor and signaling a sensor specific signal (e.g., specific frequency and/or specific modulation).

Accordingly, remote device 32 or 48 should acquire the ability to differentiate among signals associated with different sensors. The latter technology is routinely employed in smart card reading machines, which are able to differentiate among and identify radio signals generated by different cards, according to their frequencies and modulations.

In any case, display 36 may be used to report the remaining (or exhausted) absorbent capacity of the tampon, in, for example, percents.

In a preferred embodiment of the invention all radio communications are limited to a short distance (e.g., 10–30 cm), such that a system used by one user will not accidentally cross communicate with a system of another user.

Figure 3:
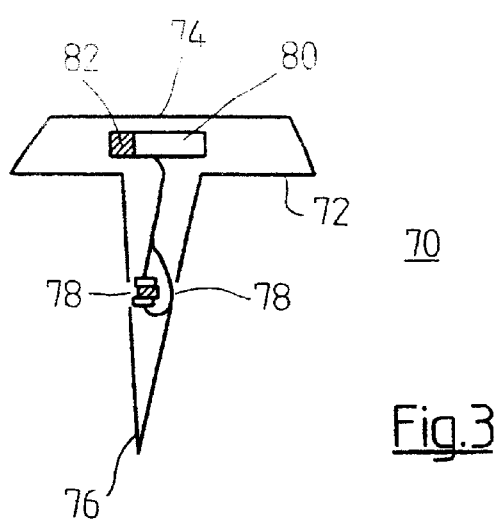
FIG. 3 is a simplified schematic depiction of a tampon wetness detection system according to another embodiment of the present invention.

With reference to FIG. 3, according to another embodiment of the present invention provided is a tampon wetness detection system 70.

System 70 includes a housing 72. Housing 72 has a distal end 74 and a proximal end 76. Proximal end 76 of housing 72 is shaped and dimensioned insertable into a distal end of a tampon (not shown in FIG. 3). Proximal end 76 of housing 72 is fluid permeable. In the example given in FIG. 3 housing 72 is shaped like a thumb tack, which is insertable into the distal end of a tampon. The fluid permeability of end 76 is effected by forming end 76 with openings 78.

In its minimal configuration system 70 further includes a radio frequency identification device 80 implemented in housing 72 and including a transmitter 82, a conductive wetness sensor 84 situated in proximal end 76 of housing 72 and being in electrical communication with device 80, a remote-reporting device 32 (shown in FIG. 2) including a receiver 34 for receiving a radio signal concerning the wetness of the tampon from device 16, and a reporting mechanism for reporting a user of the wetness of the tampon.

The preferred features described with respect to system 30 above suit also system 70 and are considered as if fully set forth herein with respect to system 70.

Both systems 30 and 70 according to the present invention enjoy a major advantage as compared with the prior art since an indication of the remaining tampon absorbent capacity is remotely obtainable and therefore the system does not call for intimate inspection like prior art systems.

System 70 enjoys a particular advantage since it is implementable with existing conventional tampons.

In a broader sense, the sensor employed within the tampon according to the present invention is adapted of detecting one or more substances such as, but not limited to, menses, blood, water, sugars, minerals, ions, salts, proteins, toxins, microorganisms, and the like, or one or more parameters, such as, but not limited to, temperature, wetness, pH. Miniaturized temperature, pH and other ions or salt sensors are well known in the art. For example, a temperature sensor is adapted at sensing a heat magnitude and converting it into an electrical parameter (e.g., resistance, voltage, etc.) of a magnitude corresponding to the heat. Thermistors thus operating are distributed, for example, by Beta Therm Cat. #1K7A1. A glucose sensor according to the present invention is preferably a glucose oxidase based glucose sensor which includes a potentiostat and an electronic chip for quantifying the glucose level in the blood sample. The operation of these components is will known in the art. Prior art glucose sensors are distributed by, for example, LifeScan Inc. and MediSense Inc. USA. Other sensors are also known in the art and can be miniaturized to fit into a tampon.

Figure 4:
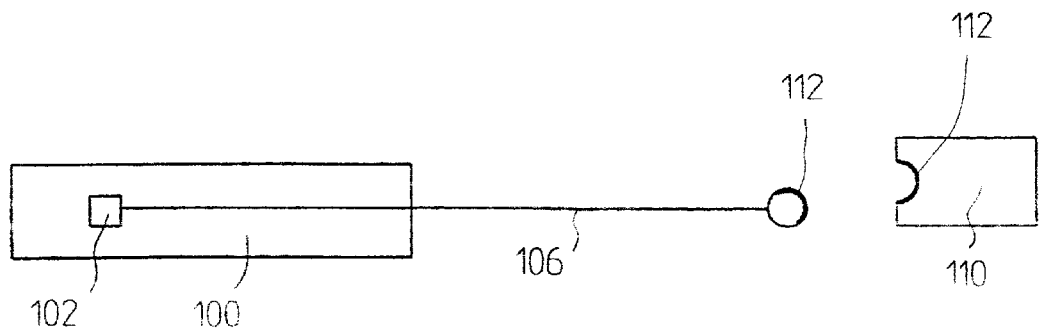
FIGS. 4 and 5 are simplified schematic depiction of tampon detection systems according to additional embodiments of the present invention.

As shown in FIG. 4, according to the present invention there is provided a tampon assembly which includes an absorbent body 100, at least one sensor 102 for sensing a substance or a parameter as described above and a radio frequency identification device 104 which includes a transmitter for reporting. Device 104 is engaged at the end of the tampon string which, in this case, includes a conductive wire 106 electrically communicating between sensor 102 and device 104. Device 104 may be formed detachable from wire 106 and therefore reusable via a connector, e.g., a connector integral to the string.

Figure 5:
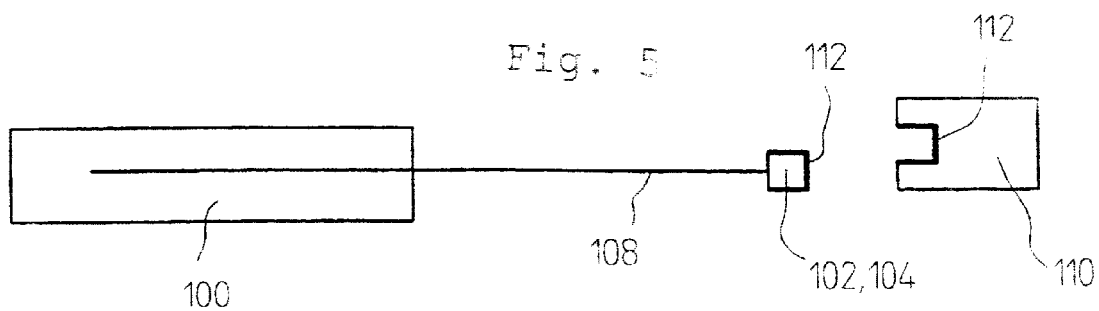

As shown in FIG. 5, if a capillary string 108, preferably laminated on the outside, is used, sensor 102 can be integrated with device 104, wherein body fluid samples are delivered to sensor 102 via string 108. In this case, the sensor as well as the transmitter can be made detachable and reusable via a connector, e.g., a connector integral to the string.

In both cases, device 104 and sensor 102 can be powered via a power source attached, for example, to the underwear of the user. In both cases a reporting device 110 can retrieve the information from device 104, as further described hereinabove, or by a direct electrical contact therewith. In the latter case, terminals 112 are provided so as to effect such direct contact and the shape of the devices 104 and 110 are selected compatible therefor. In this case, device 110 can also be attached to the underwear or skin of the user.

Device 110 preferably includes an internal memory module which records the retrieved data. The data can be downloaded to a computer for analysis. Additional features thereof are described hereinabove.

According to a preferred embodiment of the present invention, the information or data retrieved by device 110 is timed and dated. To this end, either device 104 and/or device 110 are supplemented with a timer/date module.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A tampon assembly comprising:
   (a) an absorbent body insertable into a vagina;
   (b) a radio frequency identification device being implemented in contact with said body, said radio frequency identification device including a transmitter; and
   (c) a sensor being implemented in intimate contact with said body, said sensor being in electrical communication with said radio frequency identification device, such that when said sensor senses a substance or parameter said radio frequency identification device is operable.

2. The assembly of claim 1, wherein said radio frequency identification device is selected from the group consisting of passive radio frequency identification device and active radio frequency identification device.

3. A tampon wetness detection system comprising:
   (a) a tack-shaped housing having a distal end and a proximal end, said proximal end being shaped and dimensioned for insertion into a distal end of an absorbent body insertable into a vagina, said proximal end of said housing being fluid permeable;
   (b) a radio frequency identification device being implemented in said housing, said radio frequency identification device including a transmitter;
   (c) a conductive wetness sensor being in said proximal end of said housing and in electrical communication with said radio frequency identification device, such that when said conductive wetness sensor senses wetness said radio frequency identification device is operable; and
   (d) a remote-reporting device including a receiver for receiving a radio signal concerning the wetness of the absorbent body from said radio frequency identification device and further including a reporting mechanism for reporting a user of the wetness of the absorbent body.

4. A tampon assembly comprising:
   (a) an absorbent body insertable into a vagina;
   (b) a radio frequency identification device being implemented in contact with said body, said radio frequency identification device including a transmitter; and
   (c) a sensor being implemented in contact with said body, said sensor being in electrical communication with said radio frequency identification device, such that when said sensor senses a substance or parameter said radio frequency identification device is operable.

5. The tampon assembly of claim 4, wherein said sensor is in intimate contact with said absorbent body and further wherein said radio frequency identification device communicated with said sensor via a wire.

6. The tampon assembly of claim 4, wherein said sensor communicates with said absorbent body via a capillary string and further wherein said sensor and said radio frequency identification device are integrated into a single device connected to said string.

7. A system for detecting a substance or a parameter of a body fluid comprising:
   (a) a tampon assembly comprising:
      (i) an absorbent body insertable into a vagina;
      (ii) a radio frequency identification device being implemented in contact with said body, said radio frequency identification device including a transmitter; and
      (iii) a sensor being implemented in contact with said body, said sensor being in electrical communication with said radio frequency identification device, such that when said sensor senses a substance or parameter said radio frequency identification device is operable; and
   (b) a reporting device including a receiver for receiving a radio signal from said radio frequency identification device and further including a reporting mechanism for reporting a user of the wetness of the tampon.

8. The system of claim 7, wherein said sensor is in intimate contact with said absorbent body and further wherein said radio frequency identification device communicates with said sensor via a wire.

9. The system of claim 7, wherein said sensor communicates with said absorbent body via a capillary string and further wherein said sensor and said radio frequency identification device are integrated into a single device connected to said string.

* * * * *